United States Patent
Foong et al.

(10) Patent No.: US 11,250,318 B2
(45) Date of Patent: Feb. 15, 2022

(54) METHOD AND/OR SYSTEM FOR MAGNETIC LOCALIZATION

(71) Applicants: Singapore University of Technology and Design, Singapore (SG); Massachusetts Institute of Technology, Cambridge, MA (US)

(72) Inventors: Shaohui Foong, Singapore (SG); Faye Wu, Cambridge, MA (US)

(73) Assignees: Singapore University of Technology and Design, Singapore (SG); Massachusetts Institute of Technology (MIT), Cambridge, MA (US)

(*) Notice: Subject to any disclaimer, the term of this patent is extended or adjusted under 35 U.S.C. 154(b) by 1297 days.

(21) Appl. No.: 14/889,578

(22) PCT Filed: May 7, 2014

(86) PCT No.: PCT/SG2014/000200
§ 371 (c)(1),
(2) Date: Nov. 6, 2015

(87) PCT Pub. No.: WO2014/182246
PCT Pub. Date: Nov. 13, 2014

(65) Prior Publication Data
US 2016/0086080 A1 Mar. 24, 2016

Related U.S. Application Data

(60) Provisional application No. 61/820,472, filed on May 7, 2013.

(51) Int. Cl.
*G06N 3/08* (2006.01)
*G01B 7/00* (2006.01)
(Continued)

(52) U.S. Cl.
CPC ............... *G06N 3/08* (2013.01); *A61B 5/062* (2013.01); *A61B 5/7264* (2013.01); *G01B 7/003* (2013.01); *G06N 3/063* (2013.01)

(58) Field of Classification Search
CPC .................................. G06N 3/08; G06N 3/063
See application file for complete search history.

(56) References Cited

U.S. PATENT DOCUMENTS 4,511,985 A * 4/1985 Inaba ..................... B25J 9/1612
318/568.13
6,263,230 B1 * 7/2001 Haynor .................. A61B 5/062
128/899

(Continued)

FOREIGN PATENT DOCUMENTS

JP 05-035709 2/1993
JP 2002-529133 A 9/2002
(Continued)

OTHER PUBLICATIONS

International Search Report and Written Opinion for Application No. PCT/SG2014/000200 dated Jul. 22, 2014.
(Continued)

*Primary Examiner* — Alexey Shmatov
*Assistant Examiner* — Ahsif A. Sheikh
(74) *Attorney, Agent, or Firm* — Lerner, David, Littenberg, Krumholz & Mentlik, LLP

(57) ABSTRACT

A method of real time magnetic localization comprising: providing an artificial neural network field model that is calibrated and optimized for a predetermined magnet; receiving signals from one or more magnetic sensors; and solving the location of the magnet using the model based on the signals.

22 Claims, 6 Drawing Sheets

(51) Int. Cl.
*A61B 5/06* (2006.01)
*A61B 5/00* (2006.01)
*G06N 3/063* (2006.01)

(56) References Cited

U.S. PATENT DOCUMENTS

| | | | |
|---|---|---|---|
| 6,553,326 B1 | 4/2003 | Kirsch et al. | |
| 8,862,200 B2* | 10/2014 | Sherman | A61B 90/39 600/407 |
| 2004/0138560 A1* | 7/2004 | Paladini | G01S 7/52044 600/437 |
| 2006/0251303 A1* | 11/2006 | He | G06K 9/0057 382/128 |
| 2011/0224565 A1* | 9/2011 | Ong | A61B 5/742 600/509 |
| 2014/0032463 A1* | 1/2014 | Jin | G06N 3/0454 706/25 |
| 2014/0085185 A1* | 3/2014 | Sarwar | G06F 3/011 345/156 |

FOREIGN PATENT DOCUMENTS

| | | |
|---|---|---|
| JP | 2003-530557 A | 10/2003 |
| WO | 98049938 A1 | 11/1998 |
| WO | 01077701 A1 | 10/2001 |

OTHER PUBLICATIONS

International Written Opinion for Application No. PCT/SG2014/000200 dated May 26, 2015.
M.Maeda, Three-dimensional spatial coordinate reading systems using magnetic sensor. Fiscal 1995. (The Ministry of Education, Science and Culture S)., Three-dimensional spatial coordinate reading systems using magnetic sensor. Fiscal 1995. No. 06452232, 1996, pp. 1-75 (English translation of Chapter 1 Introduction is provided herewith.).
Maenaka et al., "A study of three-dimentional position sensing system with solid-state magnetic sensor and neural processing", Technical Digest of the 12th Sensor Symposium, 1994, pp. 199-202.
Maenaka et al., "Application of multidimensional magnetic sensors—Position and Movement Detection—", Sensors and Materials, vol. 8, No. 1 (1996) 033-046.
Maenaka et al., "Position and MOvement Detection System for Small Area", Proceedings of the International Symposium, Microsystems, Intelligent Materials and Robots, Sep. 27-29, 1995, Sendai, Japan, pp. 618-621.
Shimizu et al., "Detection of Bending Angle for Human Finger", Tehnical Digest of the 13th Sensor Symposium, 1995, pp. 233-236.
Takashi Nagaoka et al., Development and Application of a Three-dimensional Position Sensor Using a Permanent Magnet, Transactions of Japanese Society for Medical and Biological Engineering, vol. 42 No. 4, Dec. 10, 2004, pp. 100-106 (English Abstract provided.).
Tomoki Okazaki et al., "Navigation system of a catheter using magnetic sensors neural network", Proceedings of the Bioengieering Conference, vol. 16th, Jan. 21, 2004, p. 363-364.
International Preliminary Report on Patentability for Application No. PCT/SG2014/000200 dated Aug. 19, 2015.

* cited by examiner

METHOD AND/OR SYSTEM FOR MAGNETIC LOCALIZATION

CROSS REFERENCE TO RELATED APPLICATIONS

This application is a national phase entry under 35 U.S.C. § 371 of International Application No. PCT/SG2014/000200, filed May 7, 2014, published in English, which claims the benefit of the filing date of U.S. Provisional Patent Application No. 61/820,472 filed May 7, 2013, the disclosures of which are hereby incorporated herein by reference.

FIELD

The present invention relates to a method and/or system for magnetic localization.

BACKGROUND

Recent advancement in miniaturization and sensitivity in magnetic sensor technology has motivated emerging applications of magnetic tracking and localization techniques in robotics and mechatronics systems. Magnetic field-based positioning systems are compact, low-cost, robust, non-invasive, unobtrusive, energy-efficient, and safe. Magnetic localization involves capitalizing on sensitivity of modern solid-state sensors to detect minute changes in the measured vector magnetic flux density (MFD) due to relative positional changes between the magnetic source and sensors. By affixing the source (or the sensor) onto the moving target and referencing the known position of the sensor (or source), the instantaneous orientation and position of the target can be extracted through active measurement and monitoring of the sensor.

This determination, however, requires a field model, a function that relates position to MFD, and the most commonly used model is the magnetic dipole (MD) model.

One of the key advantages of magnetic field-based localization is that passive magnetic sources exist. This not only allows the localization target to be completely un-tethered but also eliminates the requirement of a power source to generate the field. This results in a very compact sensing system on the target which consists of only a permanent magnet. In addition to sensing across non-ferromagnetic mediums including air and the human body, magnetic fields are invariant to temperature, pressure, radiation and other environmental factors, which make them an excellent choice for tracking and localization applications in medical environments. It is employed in tracking of tongue motion during speech-language therapy, assessing the location of the probe during endovascular catheterisation, assisting in robotic capsule endoscopy and for anatomical mapping and motility studies of the digestive system. The non-contact nature of field-based localization is harnessed in industrial applications for high accuracy sensing as well as feedback control of actuators. In the realm of robotics, it is integrated in UAVs to locate power lines for perching and an integral component of the magneto-elastomeric force sensor in a running quadruped.

Magnetic localization involves tackling the inverse problem and since explicit expression for the inverse model is not available, the forward model (the field model) is used instead. This is achieved by using a nonlinear optimization algorithm to minimize the deviation between measured and modelled magnetic field. A significant proportion of literature on magnetic localization uses the MD model. The issue with the MD model is that it does not take into account the geometrical shape or magnetization of the physical magnet. Due to its formulation, while it is able to adequately characterize the magnetic field at large distances from the source, the model accuracy rapidly deteriorates as it approaches the surface of the magnet. The distributed multi-pole (DMP) model, which consists of a spatial array of dipoles, was conceived to address the shortcomings of the single dipole model. However, it requires a fairly involved and manual process to determine a suitable spatial dipole array.

Thus for many medical applications where the source and sensors are in close proximity, these two models are either not adequate or too tedious to perform high accuracy model-based tracking. While finite element analysis can provide a more accurate location, it is not feasible for real-time localization.

SUMMARY

In general terms the invention proposes using a neural network trained for a given magnet, to determine the location of the magnet using the field data from a series of magnetic sensors. The advantage to that accuracy may be improved when the source and sensors are in close proximity.

In a first specific expression of the invention there is provided a method of real time magnetic localization according to claim 1.

In a second specific expression of the invention there is provided a system for real time magnetic localization of an in vivo device or a medical instrument configured for insertion into a patient according to claim 11.

Embodiments may be implemented according to any of claims 2 to 10 or 12 to 15.

BRIEF DESCRIPTION OF THE DRAWINGS

One or more example embodiments of the invention will now be described, with reference to the following figures, in which.

DETAILED DESCRIPTION

Figure 1:
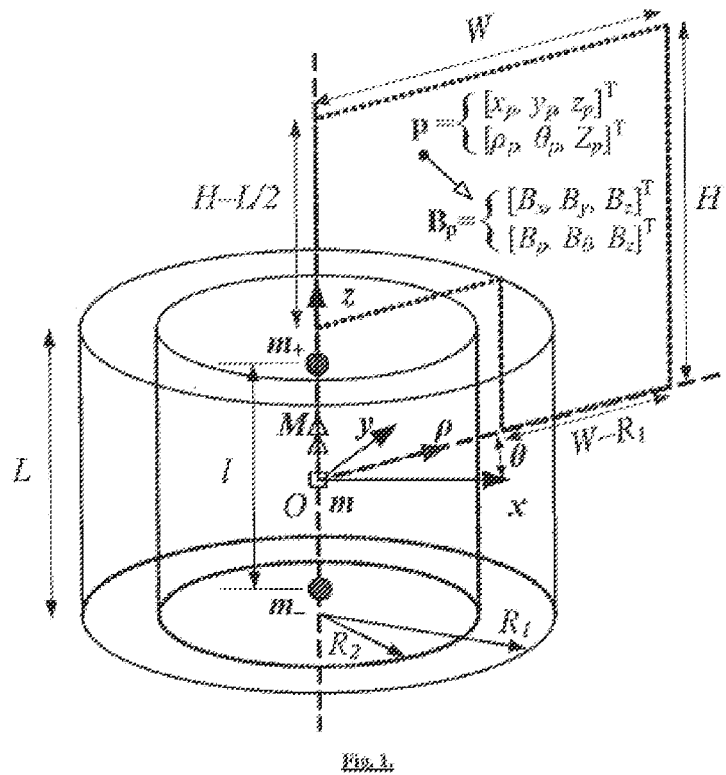
FIG. 1 is a schematic diagram showing the coordinate system for axisymmetric object and magnetic dipole models.

Artificial neural networks (ANNs) are mathematical models that are inspired by the functional structure of biological neural networks. Paired with supervised learning, back-propagation ANNs can be engaged to infer function from observations and are particularly useful where the underlying function is overly complex or unknown. Compared to other methods of function approximation, the order of the approximation is easily tuned through the architecture of the ANN. While the magnetic field of an object satisfies Maxwell's Equations, there are a multitude of parameters as well as physical imperfections that affect the magnetic field of a magnetic source.

What we are attempting to do is to relate (or map) an arbitrary set of inputs to another set of outputs (here we relate position to magnetic field measurements). This is also referred to as functional fitting. Some methods include straightforward Look-Up Table (LUT) methods, conventional least squares (LS) using basis functions of polynomials, sinusodials, etc and artificial neural networks (ANN). Both the LUT and LS approaches are more extensively used due to their simplicity, but we have identified that ANNs are more adaptable when mapping multiple inputs and outputs. In addition, adding hidden layers or nodes has minimal effect on computation time as only arithmetic operations are required during real-time operation of ANN.

Look Up Tables:

A LUT is a structured data where the location within this data structure contains pre-computed value of the desired output. These locations (known as lattice points) are discrete in nature and computation of the output for non-lattice points are obtained using interpolation methods. An issue with using LUT with interpolation is the significant increase in complexity in constructing the LUT and performing successive interpolation as the number of independent field measurements increases. For mappings requiring more than 3 axes of independent field measurement, this method becomes memory intensive due to the large array of pre-computed data and requirement of numerous interpolating operations.

Least Squares Models:

Another commonly used method in data fitting is least squares. The best fit in the least-squares sense minimizes the sum of squared residuals. A residual is defined as the difference between a desired observed value and the value provided by a model. A model can be linear or nonlinear and for the single input case, some of the well-known models are polynomial or sinusoidal (Fourier series). Like LUT, it is not easily scalable with increased inputs and higher order models. Moreover, these models are limited to a single output. For multiple outputs, independent multiple models must be used.

Artificial Neural Networks:

As mentioned an artificial neural network is a mathematical model that tries to mimic the structure and functional aspects of biological neural networks. Paired with supervised learning, back propagation ANNs can be trained to fit a desired set of inputs to a corresponding set of outputs by iteratively adjusting the weighting coefficients in the network. A commonly used cost function is the mean-squared error which tries to minimize the average squared error between the network's output desired target values over all data pairs. We have identified two approaches in obtaining the minimum: Gauss-Newton algorithm and the gradient descent method. However, the Levenberg-Marquardt algorithm, which interpolates between both methods, may be employed. Neural networks are scalable as the general training algorithm is not dependent on the number of inputs and outputs. The order of the network is easily controlled by the number of hidden layers and number of hidden nodes within each layer.

I. Magnetic Field Modelling

In the source-free and current-free space (J=0) around a stationary magnetic object, the magnetic field (or flux density) B satisfies the two magnetostatic equations:

$$\nabla \times H = 0 \qquad (1)$$

$$\nabla \cdot B = 0 \qquad (2)$$

where H is the magnetic field intensity defined by the magnetic flux density (MFD), B. If the object has a magnetization of M, the relationship between H and B is expressed by $$H = B/\mu_0 - M \qquad (3)$$

where $\mu_0$ is the magnetic permeability of free space. The vector B at a point in space $x=[x\ y\ z]^T$ can be expressed as a gradient of the magnetic scalar potential $\phi$:

$$B(x)[B_x\ B_y\ B_z]^T = -\mu_0 \nabla \Phi \qquad (4)$$

The solution of the potential $\phi$ is obtained from the Poisson equation, given and approximated by $$\Phi(x) = -\frac{1}{4\pi} \int \frac{\nabla \cdot M(x')}{|x-x'|} d^3 x' \approx \frac{m \cdot x}{4\pi |x|^3} \qquad (5)$$

where primes denote coordinates of the magnetic material and $m = \int M d^3 x'$ is the magnetic moment. The combination of (4) and approximation in (5) forms the basis for the ubiquitous magnetic dipole (MD) model, which assumes M is well-behaved, localized and more importantly, x>>x'.

A. Dipole Field Modelling

For an axisymmetric (about z-axis) magnetic object with its M coinciding with its axis of symmetry $\hat{z}$, as illustrated in FIG. 1, the magnetic field produced by this object can be approximated by a dipole (yellow square) at the origin O. Without loss of generality, the axisymmetric geometry is represented by an annular cylinder with length L and outer and inner radii of $R_1$ and $R_2$ respectively. The origin is set to coincide with the centroid of the annular cylinder. Hence, the magnetic flux density at point p due to this dipole with a dipole moment of $m=m\hat{z}$ at O is $$B_p\{MD\} = \frac{\mu}{4\pi}\left[\frac{3p(m \cdot p)}{|p|^5} - \frac{m}{|p|^3}\right] \qquad (6)$$

An alternative method of modelling magnetic fields is the distributed multi-pole (DMP) model, which involves multiple discrete source and sink poles. For the magnetic object in FIG. 1, the corresponding magnetic flux density at point p due to a discrete pair of source (+) and sink (−) poles (red circles) each with strength m and separated by the distance l is $$B_p\{DMP\} = \frac{m\mu}{4\pi}\left[\frac{p-m_-}{|p-m_-|^3} - \frac{p-m_+}{|p-m_+|^3}\right] \quad (7)$$

where $m_+=[0\ 0\ l/2]^T$ and $m_-=[0\ 0\ -l/2]^T$ are the spatial location of the source and sink, respectively. The pole distance is limited by $0<l<L$ to prevent singularity at the magnet surface. To determine the unknowns of m and l of the MD and DMP models, computing the minimum of the following error function E is required:

$$E = \Sigma \|B_{model}\{MD,DMP\} - B_{exp}\|^2 \quad (8)$$

where $B_{exp}$ is the experimentally obtained field data. Again, it can be observed that the shape and size of the magnet are not factored into the dipole models.

Since the radiating field of an axisymmetric object, with magnetization coincident to the axis of symmetry, is also axisymmetric, describing $B_p$ in cylindrical coordinates $[B_\rho\ B_\theta\ B_z]^T$ is advantageous as $B_\theta = 0$. Therefore, the entire 3D magnetic vector field around the object can be completely characterized by only 2 variables ($B_\rho$ and $B_z$) in the singular radial slice demarcated by the dashed red-lines in FIG. 1. $B_p$ can be converted from cylindrical (CYL) coordinates to Cartesian (CAR) coordinates and vice versa:

$$[(-1)^w\sqrt{B_x^2+B_y^2}\ 0\ B_z]_{CYL}^T = [B_\rho \cos\theta\ B_\rho \sin\theta\ B_z]_{CAR}^T \quad (9)$$

where w is used to select the correct sign of $B_\rho$ and is defined as:

$$w = \begin{cases} 0 & \text{if sign}(x) = \text{sign}(B_x) \text{ or sign}(y) = \text{sign}(B_y) \\ 1 & \text{otherwise} \end{cases} \quad (10)$$

For completeness, converting between cylindrical and Cartesian coordinates for p is $$[\sqrt{x^2+y^2}\ 0\ z]_{CYL}^T = [\rho\cos\theta\ \rho\sin\theta\ z]_{CAR}^T \quad (11)$$

B. Artificial Neural Network (ANN) Field Modelling

Figure 2A:
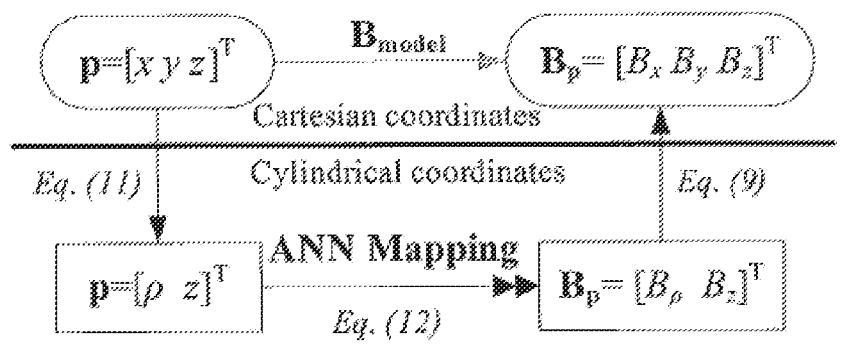
FIG. 2*a* is a flow diagram if an ANN field modelling process according to an example embodiment.
Figure 2B:
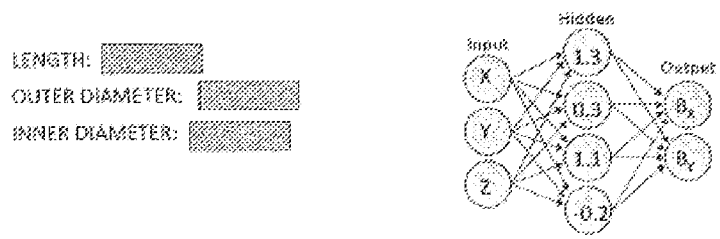
FIG. 2*b* is a representation of a GUI for automated ANN field modelling where the user inputs the magnet dimensions on the left and via field measurements, the coefficients of the ANN field models are generated on the right.

By exploiting the axisymmetry of the magnetic field and operating in cylindrical coordinates, an artificial neural network (ANN) can be harnessed to model fields with high accuracy and low computational overheads. A flowchart outlining the ANN based magnetic field modelling process is illustrated in FIG. 2. Here the spatial coordinate of interest p, expressed in Cartesian format, is transformed into cylindrical coordinates with (11). $\theta$ and $B_\theta$ are omitted because the field is axisymmetric. This reduces the required ANN mapping to a simple 2-input-2-output network architecture, in contrast to a potential 3-input-3-output ANN architecture when operating in Cartesian coordinates. After evaluating the ANN estimated $B_\rho$ and $B_z$, $B_p$ is transformed back into Cartesian format using (9).

Back propagation ANNs (with architecture of j hidden layers, k hidden nodes per hidden layer) can be trained with Levenberg-Marquardt supervised learning algorithm to fit a desired set of inputs to a corresponding set of outputs by iteratively adjusting the weighting coefficients in the network to minimize the root mean squared error (RMSE) over N data pairs. In this case, the inputs are the two spatial cylindrical coordinates $\rho$ and z, and the outputs are the two non-zero magnetic flux densities $B_\rho$ and $B_z$. Mathematically, the neural network can be represented as $$y_k = g\left(\sum_{j=0}^{M}\omega_{kj}^{(2)} g\left(\sum_{i=0}^{d}\omega_{ji}^{(1)} x_i\right)\right) \quad (12)$$

where $g(\circ)$ is the activation function, $\omega$ is the weight function, $x_i$ is the $i^{th}$ input ($\rho,z$) and $y_k$ is the $k^{th}$ output ($B_\rho$, $B_z$). The number in parenthesis signifies the layer. The RMSE, which is used for ANN and dipole model evaluation, is expressed by $$RMSE = \sqrt{\frac{1}{N}\sum_{v=1}^{N}\left[(B_\rho - \hat{B}_\rho)^2 + (B_z - \hat{B}_z)^2\right]} \quad (13)$$

where v ($1 \le v \le N$) is an integer representing the training set index. In order to map spatial positions to magnetic flux densities, the selected 'L' shaped domain (the area in FIG. 4 surrounding the PM) is discretized into a uniform spatial grid to generate N data sets. If the spatial spacing in the grid is d (d may be optimised for accuracy verses computation effort eg: 0.1 mm), N is related to the other spatial variables via the following expression $$N = 1 + (W+H)/d + (WH-R_1L/2)/d^2 \quad (14)$$

C. Model-Based Localization

With a magnetic field model, the position of the magnetic sensor relative to the magnetic source can be determined by assigning a cost function C to be the difference between the observed/measured magnetic field and the model (DM, DMP, ANN) predicted field. For a sensor located at $x_S$, this can mathematically be expressed as follows:

$$C = \Sigma \|B_{model}(x_S) - B_{measured}\|^2 \quad (15)$$

By minimizing this cost function through an iterative non-linear least-squares optimization, the relative position of the sensor can be estimated from the field measurement.

II. Experimental Investigation & Discussion

Figure 3:
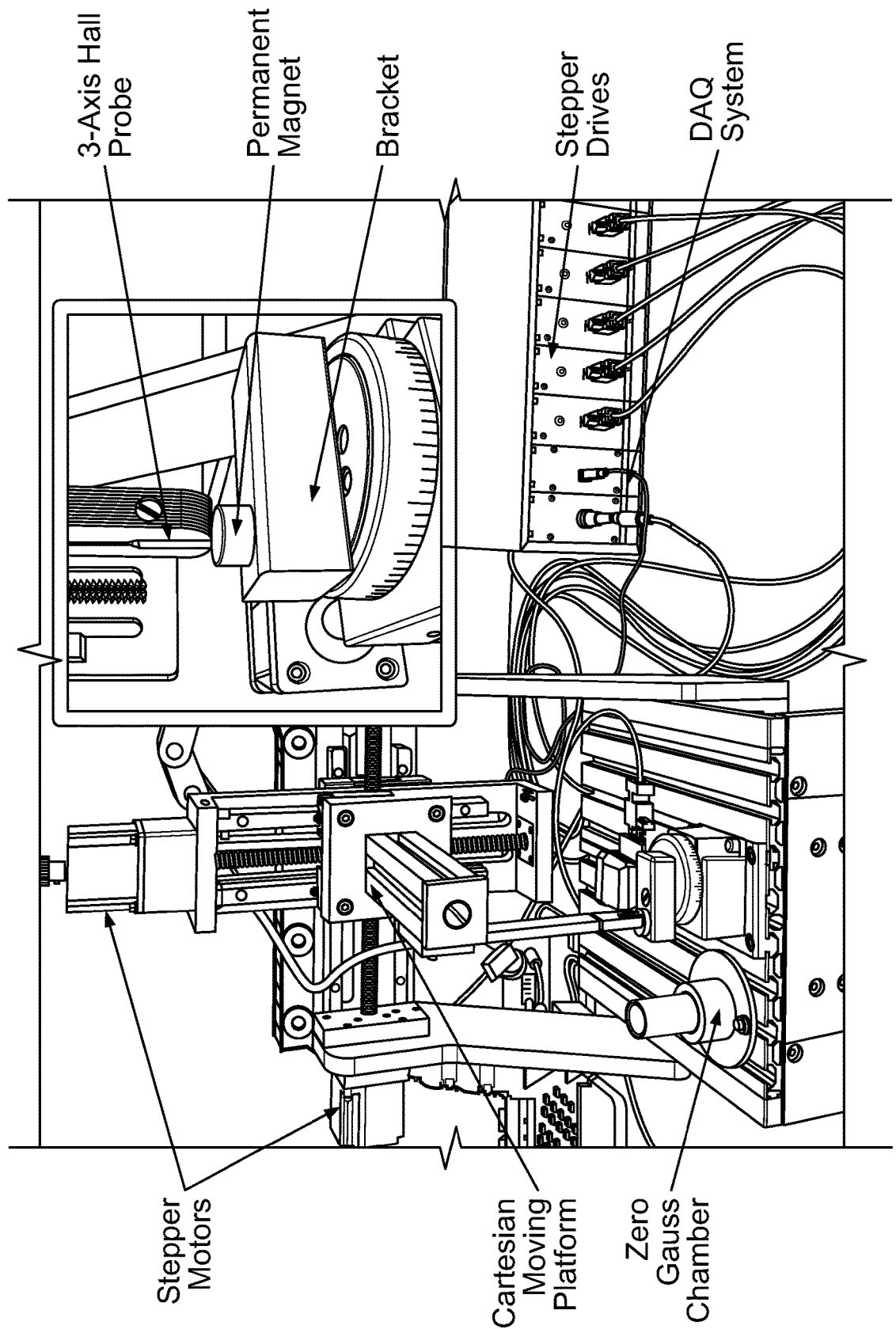
FIG. 3 is a photo of an Experimental setup of SENIS MMS-1-R magnetic field mapping system during scanning.

FIG. 3 shows a MMS-1-R magnetic field mapping system (SENIS GmbH, Zurich, Switzerland) which was used to obtain experimental magnetic field data of cylindrical magnets for evaluation of the ANN and dipole based field models. These experimentally derived models were then utilized for positional tracking analysis. The MMS-1-R consists of an xyzθ Cartesian moving platform (resolution of 10 μm) on which a 3-axis SENIS GmbH hall probe (±1000 mT, >0.1% accuracy) is mounted. The magnetic flux density measured by the hall probe is processed by the SENIS 3-axis 03A02F magnetic field transducer. A computer is connected to an NI-6212 DAQ system (National Instruments, Austin, Tex.) that controls the SSMD1 stepper motors and receives data from the transducer. The zero gauss chamber is used for calibrating the hall probe.

Two axially magnetized N52 grade Neodymium permanent magnets (KJ Magnetics, Jamison, Pa.), a solid cylinder (D86-N52) and an annular cylinder (RC44-N52), were separately mounted on the MMS-1-R using non-ferromagnetic brackets and scanned. For a specified $\theta$ slice, the probe position and $B_p$ in Cartesian coordinates were recorded at 0.1 mm increments as the hall probe moved along $\rho$. Once the boundary of the scanning domain was reached, the z position of the probe changed by 0.1 mm, and the probe retraced its movement in ρ direction. The scanning range of the 'L' shaped domain was set to four times the characteristic lengths of the magnet, meaning W=4R$_1$ and H=4(L/2), rounded to the nearest 0.1 mm. Due to physical dimensions of the probe, measurements taken closest to the magnet were 1.1 mm from the top surface of the magnet and 1.3 mm from the side. The scanning domain for the solid and annular magnet comprises of 44,475 and 44,268 data points respectively.

The magnet may be any shape. For most applications, especially clinical, the desired geometry is usually something that is axis-symmetric (cylindrical) so that it can fit into tubing/instruments. For strength, it varies from application to application but embodiments are able to take into consideration of this aspect.

The magnet may be fabricated by fusing of rare-earth magnets into one geometry. An alloy of neodymium, iron and boron to form the $Nd_2Fe_{14}B$ tetragonal crystalline structure may be used.

Figure 4:
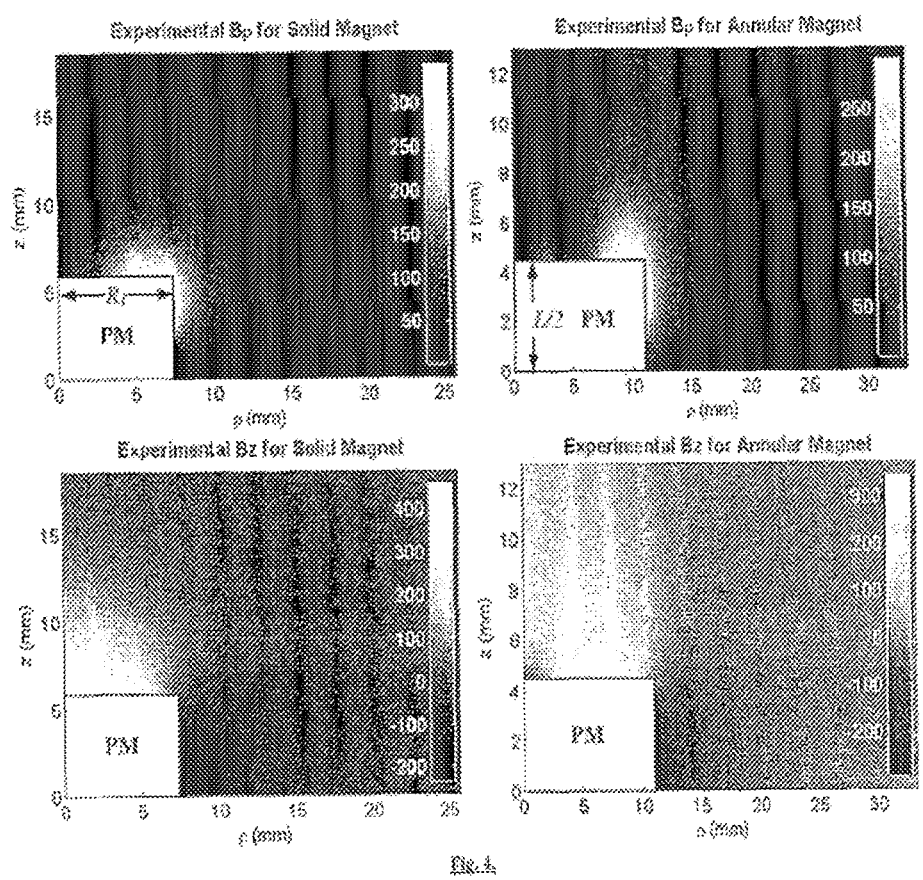
FIG. 4 is a graphed contour plot of averaged measured MFD in 'L' domain for both magnet geometries. (Units: mT). The white boxes with black border denote the physical boundary of the permanent magnet (PM)

To minimize experimental measurement errors and to verify symmetry of the magnetic fields, each magnet was scanned 8 times at random θ (θ=0°, 47°, 112°, 140°, 169°, 313°, 315°, 354°), and these 8 'L' domain slices were consolidated to create an average field (containing both $B_\rho$ and $B_z$) slice which is used to fit the dipole and ANN field models. From these 8 slices, the field variance, characterized by the standard deviation is computed for both magnets and tabulated in Table I. For both magnet shapes, the average variation among the 8 randomly obtained slices for $B_\rho$ and $B_z$ was around 2 mT, which is in the same order of magnitude with the accuracy of the hall probe. This provides experimental verification that the magnetic field of the cylindrical magnets is sufficiently axisymmetric and validates the approach to operate in cylindrical coordinates. The maximum deviation however does reach above 20 mT in certain isolated locations, which can be due to physical imperfections of the magnet. An observation to note is that the annular magnet exhibits a slightly higher maximum standard deviation in $B_\rho$ and this can be attributed to the hollow region of the magnet. The experimental contour plots of the averaged 'L' domain for both magnets are shown in FIG. 4. The plots in FIG. 4 clearly demonstrate the significant difference between the magnetic field around a solid and annular cylindrical magnetic source, which is especially evident near the surface.

TABLE I

STATISTICAL ANALYSIS ACROSS 8 'L' DOMAIN SLICES

| | Standard Deviation (mT) | | | | | |
|---|---|---|---|---|---|---|
| Magnet | $B_\rho$ | | | $B_z$ | | |
| Shape | Mean | Min | Max | Mean | Min | Max |
| Solid | 1.83 | 0.09 | 25.61 | 1.93 | 0.09 | 32.89 |
| Annular | 2.22 | 0.03 | 75.19 | 2.00 | 0.06 | 31.78 |

Figure 5:
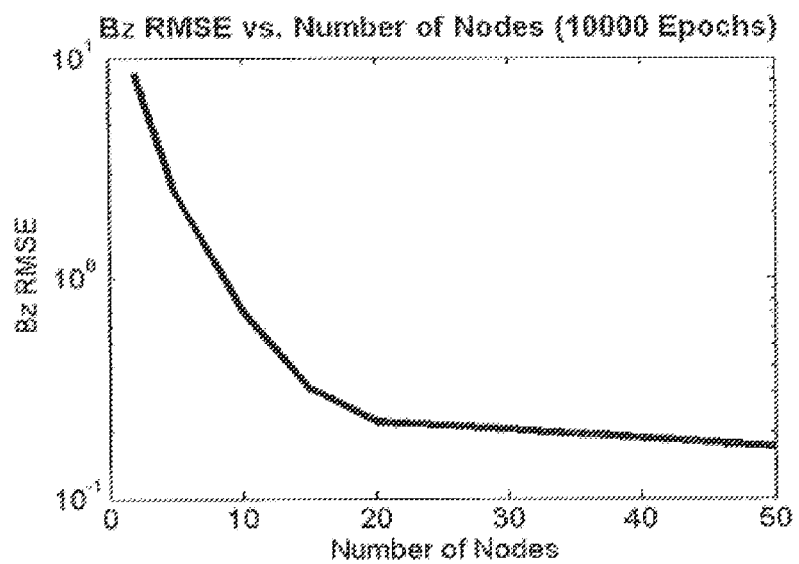
FIG. 5 is a graph of RMSE of ANN fit of Bz as a function of hidden nodes.

Using MATLAB's optimization toolbox (Mathworks, Natick, Mass.), the experimental average field slice was used to fit the dipole and multi-pole models based on Levenberg-Marquardt algorithm (LMA). The fitted parameters for the MD and DMP models, as well as the magnet parameters, are consolidated in Table II. For the ANN-based field model, the number of hidden layers was set to 1 (j=1) and the RMSE of the ANN fit was recorded for $B_z$ of the solid magnet as the number of hidden nodes k varied. The results, illustrated in FIG. 5, clearly show an asymptotic decline of RMSE once k=20 is reached. A similar feature is also present for $B_\rho$ as well as for the annular magnet. Hence a single hidden layer ANN with 20 hidden nodes is selected for field mapping.

In order to calibrate or train the system for a given magnet, the first step is to obtain a magnetic field map of the target/unknown magnet. This can be quickly and easily done by placing the magnet onto a magnetic field camera (http://www.magcam.com/). Next, by extracting the axis-symmetric field slice, using automated symmetry analysis, this slice can be used to train/fit the desired ANN model. The number of hidden nodes is slowly increased and the residue error of the fit is actively monitored. Once it is detected that the increase in the number of hidden nodes only reduces the residue error less than the minimum threshold, the procedure stops and the ANN model is complete. At each iteration, the stoppage of ANN training is also governed by standard ANN training and stopping criteria. Hence all steps are automatic except the insertion of the magnet and entering the dimensions of the magnet. The output will be the ANN field model, with all the weights/coefficients of the model available for use.

TABLE II

MAGNET SPECIFICATIONS AND FITTED MODEL PARAMETERS

| | | | | | Fitted analytical field model | | |
|---|---|---|---|---|---|---|---|
| | | Magnet | | | MD | DMP | |
| Shape | Grade | L (mm) | R$_1$ (mm) | R$_2$ (mm) | $m_{MD}$ (Am$^2$) | $m_{DMP}$ (Am) | l (mm) |
| Solid | N52 | 9.525 | 6.35 | — | 8.58 × 10$^8$ | 5.21 × 10$^8$ | 2.32 |
| Annular | N52 | 6.35 | 9.525 | 3.175 | 2.22 × 10$^8$ | 35.8 × 10$^8$ | 0.30 |

A. Comparison among Field Models

Figure 6:
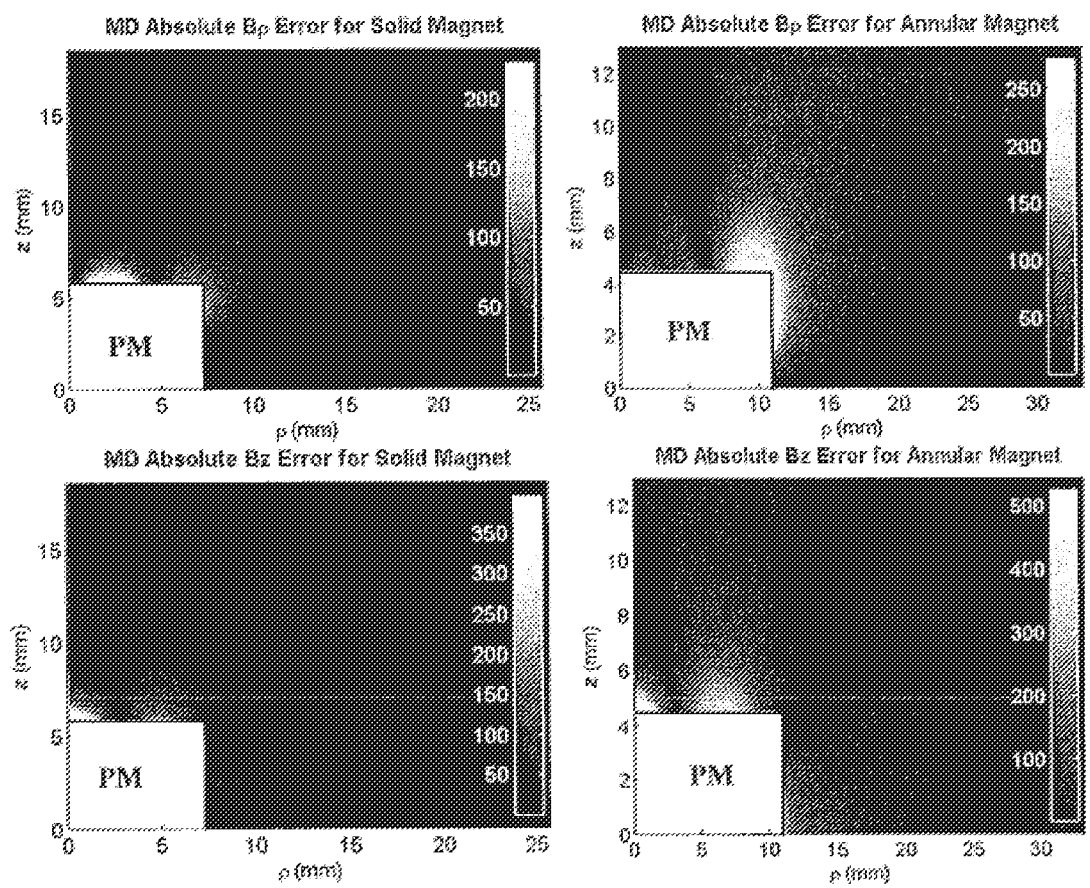
FIG. 6 is a graph of absolute error for MD field model illustrated spatially for both magnet geometries. (Units: mT)
Figure 7:
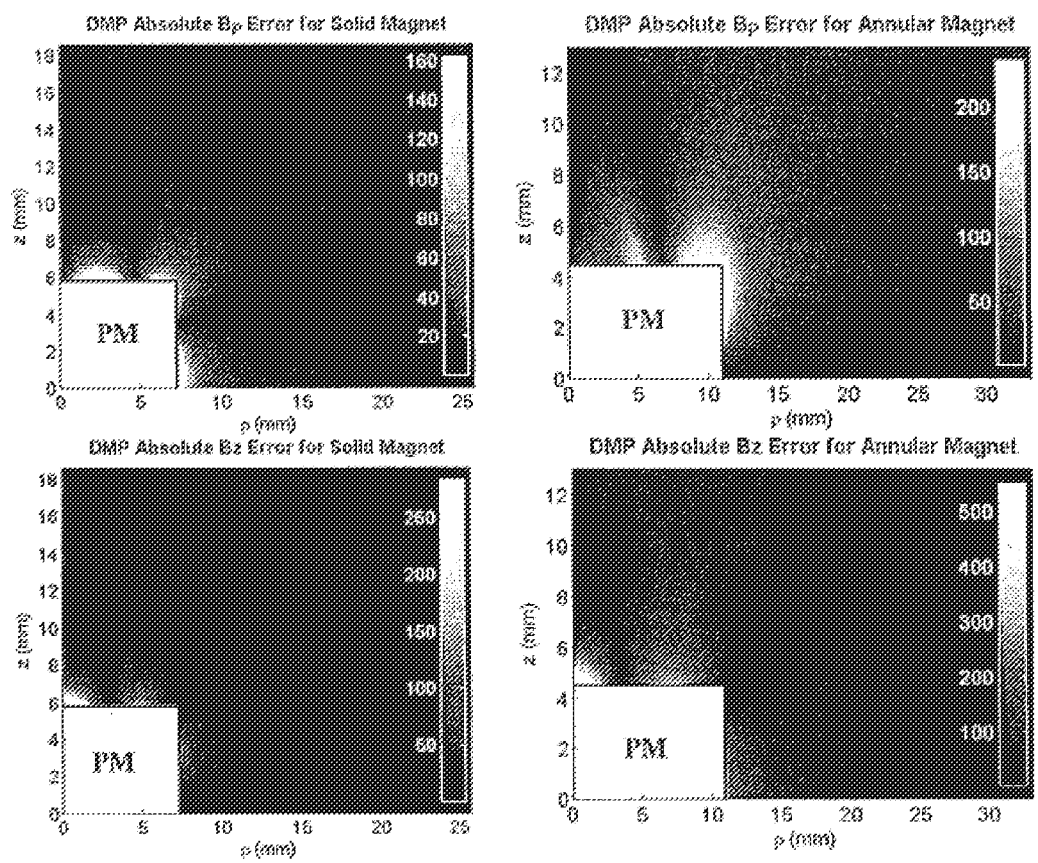
FIG. 7 is a graph of absolute error for DMP field model illustrated spatially for both magnet geometries. (Units: mT)
Figure 8:
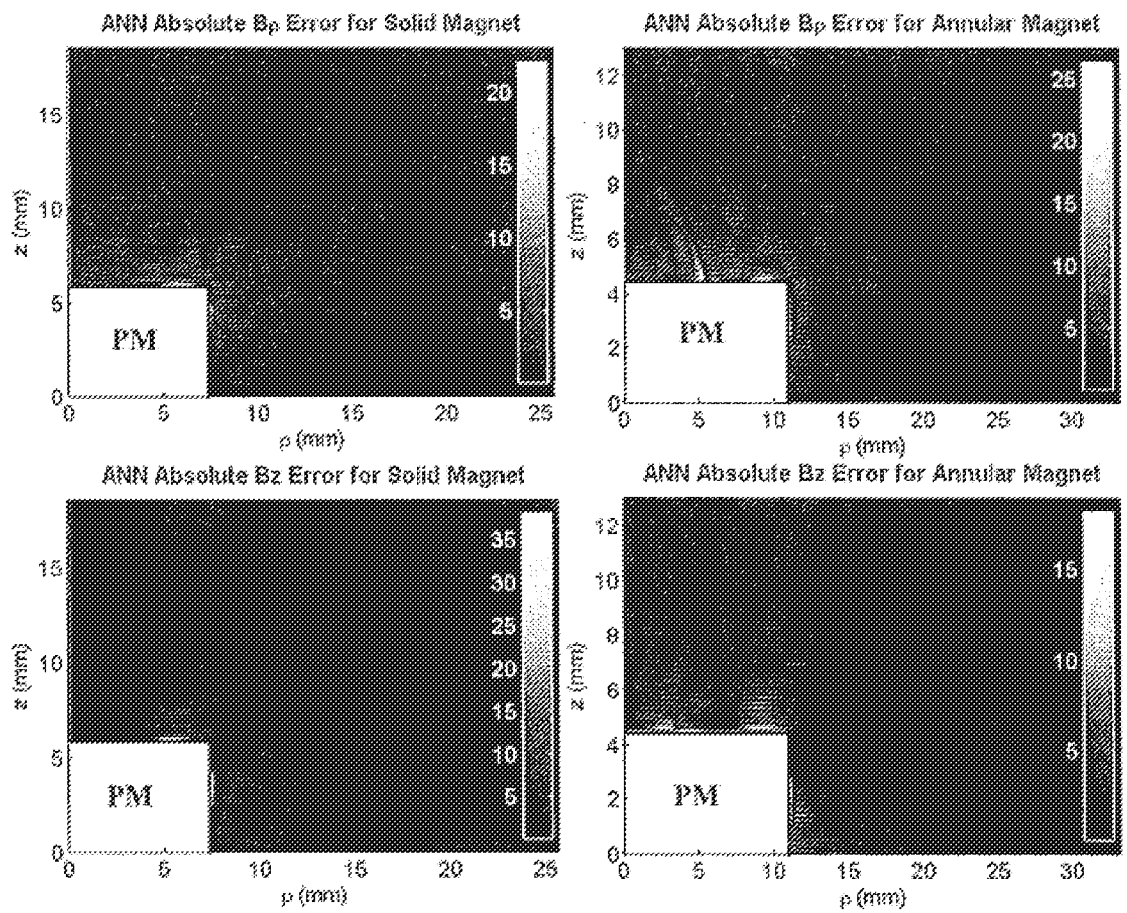
FIG. 8 is a graph of absolute error for ANN field model illustrated spatially for both magnet geometries. (Units: mT)

With the fitted parameters of the MD and DMP models in Table II, as well as the weighting coefficients of the ANN (k=20), the absolute field error between the field model prediction and actual experimental data can be computed at each spatial coordinate for both the solid and annular cylindrical magnet. The absolute field error for $B_\rho$ and $B_z$ illustrated using contour plots are shown in FIG. 6, FIG. 7 and FIG. 8 for the MD, DMP and ANN field models respectively. In FIG. 6, it can be observed that the MD model adequately represents the field at locations far from the magnet surface (error is close to zero). However, at locations near the surface (1-2 mm) of the solid magnet, the error exceeds 200 mT and 350 mT for $B_\rho$ and $B_z$ respectively. Comparing this to the experimental field values in FIG. 4, it represents a percentage error that exceeds 50%. For the annular magnet, the absolute errors are even higher (more than 250 mT for $B_\rho$ and over 500 mT for $B_z$) and more extensive as shown by the lighter areas that extend into space in the right column of FIG. 6.

Direct spatial comparison between the contour plots of FIG. 6 and FIG. 7 suggest that the DMP model, with its additional parameter I, offers an improvement over the MD model in both magnets. For the solid magnet, the absolute errors are now restricted to 160 mT and 260 mT for $B_\rho$ and $B_z$. For the annular magnet, while the peak of absolute errors of the DMP model is still comparable to the MD model, the areas of high absolute errors (lighter areas of the contour plot) have receded.

Finally FIG. 8 depicts the spatial distribution of the absolute error of the ANN field model for both geometries. There are two important observations:

- The peak absolute errors of $B_\rho$ and $B_z$ for both geometries do not exceed 40 mT at all spatial points.
- The entire 'L' domains are almost completely dark (representing low absolute errors). Only isolated light spots are present.

To facilitate further comparisons, Table III summarizes the RMSE of the various field models for the two types of magnets. As expected, the MD performed the worst with an RMSE of 9.31 mT and 27.2 mT for the solid and annular shaped magnet respectively. With the ability to adjust the separation of the dipole, the DMP model fared slightly better. The ANN model however possess an impressive RMSE of just 0.84 mT for the solid magnet (about 1 order of magnitude less than DM model) and a 0.75 mT for the annular magnet (improvement by more than 1 order of magnitude from the DM model).

From these observations, it is obvious that unlike the ANN, both the DMP and MD models are unable to adequately model the high degree of non-linearity of the magnetic field that occurs close to the magnet surface. While the DMP and MD models are highly sensitive to magnet geometry, the ANN model was unaffected.

TABLE III

COMPARISON OF RMSE ACROSS FIELD MODELS AND MAGNET GEOMETRIES

| Magnet Shape | RMSE (mT) | | | | | |
|---|---|---|---|---|---|---|
| | MD | | DMP | | ANN | |
| | $B_\rho$ | $B_z$ | $B_\rho$ | $B_z$ | $B_\rho$ | $B_z$ |
| Solid | 9.95 | 8.67 | 6.11 | 5.48 | 0.62 | 1.06 |
| | 9.31 | | 5.79 | | 0.84 | |
| Annular | 27.3 | 27.1 | 21.0 | 22.2 | 0.82 | 0.68 |
| | 27.2 | | 21.6 | | 0.75 | |

B. Trajectory Tracking Performance

Figure 9:
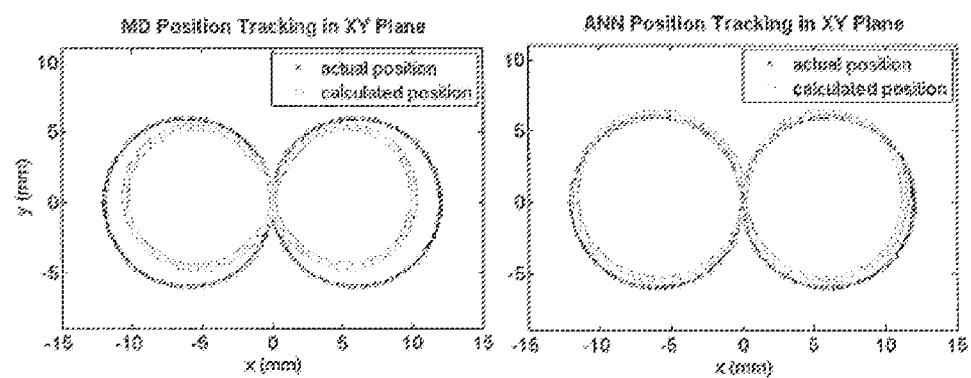
FIG. 9 is a graph of spatial tracking performance between ANN and MD field models for XY-plane figure '8' trajectory.

To evaluate the tracking performance of each of the magnetic field models, the probe on the MMS-1-R was programmed to follow a pre-determined figure '8' trajectory (radius of 6 mm) in the XY and XZ planes centered about the axial axis of the stationary solid cylindrical magnet. The Cartesian coordinates and magnetic field measurements of the probe were taken at 360 points. These field measurements ($B_x$, $B_y$, $B_z$) taken by the sensor on the probe were converted into cylindrical coordinates from Cartesian coordinates with (9). Utilizing the Levenberg-Marquardt algorithm to minimize the cost function in (15), the probe position ($\rho$, z) was estimated based on the MD, DMP and ANN models. Thereafter, Equation (9) was also used to determine the angular data $\theta$ needed to reconvert the calculated $\rho$ and z back to Cartesian coordinates (x,y,z) for comparison purposes using (11). FIG. 9 spatially illustrates and compares the tracking results. From visual comparison, the ANN outperforms the MD model as it is able to trace the figure '8' trajectory better. Statistical analysis of the tracking errors for both XY and XZ plane paths, which includes the DMP model, is summarized in Table IV.

As with the field model comparison, the ANN based trajectory tracking performed the best with average tracking errors of less than 1 mm for both paths. The MD model exhibited an average tracking error of 1.7 mm and surprisingly the DMP model faired poorer than the MD model with an average tracking error of over 2 mm. This anomaly can be attributed to the selected path which may have coincidently passed through isolated locations where the MD model outperforms the DMP model.

It is worth noting that the larger tracking errors correlate with the distance from the source as seen in FIG. 9. This is to be expected because of the reduced signal-to-noise ratio (SNR) which has a detrimental effect on model-based localization. A network of sensors may be used to boost (SNR) and improve the nonlinear least-squares optimization algorithm performance. Hence as only 3 sensing axes were used in this experiment, the tracking performance can be further improved via additional sensors.

TABLE IV

COMPARISON OF TRACKING ERROR USING DIFFERENT
FIELD MODELS FOR SOLID MAGNET

| '8' Path | Tracking Error (mm) | | | | | |
|---|---|---|---|---|---|---|
| | MD | | DMP | | ANN | |
| Trajectory | Min | Max | Min | Max | Min | Max |
| XY-plane | 1.19 | 2.31 | 0.25 | 3.47 | 0.02 | 0.88 |
| [Mean] | | 1.72 | | 2.51 | | 0.43 |
| XZ-plane | 0.33 | 2.80 | 2.98 | 1.11 | 0.20 | 1.99 |
| [Mean] | | 1.74 | | 2.14 | | 0.93 |

III. Applications

One or more embodiments may be used in a magnetic tracking system to assist in nasogastric (NG) tube insertion. Currently this procedure is done blind and X-Ray is used as definitive confirmation into the stomach. This system will consist of the nasogastric tube that is essentially unmodified except for the inclusion of a permanent magnet that is hermetically sealed at the tip of the NG tube. Each NG tube and magnet will characterized at the factory and the parameters required by the neural network modeling is embedded in a bar code that is printed on the wrapper of the NG tube.

The patient will be located beside a magnetic sensing unit and connected to a processing unit. This processing unit will consist of circuitry to acquire the electrical signals from the sensors and convert them into digital signals. The localization algorithm will be run on an embedded computer for computational speed to achieve real-time localization.

After the parameters are entered (by scanning) into the processing unit, the tube can be inserted into the patient. Due to the close proximity of the NG tube (carrying magnet) and the sensors, motion and position of the NG tube can be localized. This localization information can be broadcast over current bed-side medical screens in existing bedside monitors (where you see blood-pressure, pulse, etc).

In a further example, the contents of Singapore Patent Application No. 2013087366, "Apparatus for Real-time Non-Invasive Magnetic Field-Based Localization of Nasogastric Tube." Filed 21 Nov. 2013, are incorporated herein by reference.

Other applications include medical guidance, minimally invasive surgery, biomechanical analysis and kinesiologic studies, high precision electric motor/actuator control and robust displacement and force sensing systems.

Embodiments may incorporate specificity and imperfection of the source, which is not possible with the magnetic dipole model. This may result in a highly accurate field model that can be capitalized for precise localization. In experiments using a solid and annular magnets, the ANN based magnetic model performed 10 times better in representing magnetic field than the traditional single dipole based models, thus enabling position tracking accuracy of less than 1 mm with only 3 sensing axes.

While example embodiments of the invention have been described in detail, many variations are possible within the scope of the invention as claimed as will be clear to a skilled reader.

The invention claimed is:

1. A method of real time in vivo location determination comprising:
providing a 2-input-2-ouput artificial neural network (ANN) field model for predicting magnetic vector fields of a predetermined magnet with an axisymmetric magnetic vector field, each predicted magnetic vector field having two cylindrical prediction coordinates;
inserting a medical instrument into a patient, the medical instrument being associated with a magnetic sensor, and the magnetic sensor being associated with the predetermined magnet;
receiving, from the magnetic sensor, a sensor signal representing a measured axisymmetric magnetic vector field of the predetermined magnet, the measured axisymmetric magnetic vector field having three Cartesian measurement coordinates;
converting the three Cartesian measurement coordinates of the measured axisymmetric magnetic vector field into two cylindrical measurement coordinates;
providing the two cylindrical measurement coordinates as the two inputs to the 2-input-2-output ANN field model;
estimating- a relative position between the predetermined magnet and the magnetic sensor using the 2-input-2-output ANN field model by minimizing a cost function to produce two cylindrical coordinates as the two outputs of the 2-input-2-output ANN field model, the cost function comprising a difference between the two cylindrical measurement coordinates of the measured axisymmetric magnetic vector field and the two cylindrical prediction coordinates of each predicted magnetic vector field predicted by the 2-input-2-output ANN field model; and
converting the two cylindrical coordinates to corresponding three Cartesian coordinates for identifying a location of the medical instrument within the patient.

2. The method of claim 1 wherein the location of the medical instrument is determined when the magnetic sensor is adjacent the magnet.

3. The method of claim 2 wherein the determined location has an accuracy of less than 1 mT (RMSE) and/or a peak absolute error of less than 40 mT when the magnet is located within 25 mm from the magnetic sensor.

4. The method of claim 1 wherein the medical instrument includes the magnet, the method further comprising:
arranging the magnetic sensor on or about the patient.

5. The method of claim 1 wherein the model is based on a back propagation neural network field model trained using a Levenberg-Marquardt supervised learning algorithm.

6. The method of claim 1 further comprising selecting an order of the model and/or a number of nodes to reduce the error below a predetermined threshold.

7. The method of claim 6 wherein the order is a single hidden layer and the number of nodes is 5 to 20 hidden nodes.

8. The method of claim 1 further comprising providing a plurality of weighting coefficients for the model, wherein the weighting coefficients are pre-optimized for the predetermined magnet.

9. The method of claim 1 wherein the magnet is passive and untethered.

10. The method of claim 1, wherein the medical instrument includes the magnetic sensor, the method further comprising:
arranging the magnet on or about the patient.

11. The method of claim 1, wherein providing the ANN field model comprises:
obtaining a magnetic vector field map of the magnet;
extracting an axis-symmetric field slice from the obtained magnetic vector field map to train or fit the ANN field model; and determining a number of associated hidden nodes in accordance with a residue error based on the extracted axis-symmetric field slice.

12. The method of claim 1, wherein the cost function, 'C', is:

$$C=\Sigma\|B_{model}(x_S)-B_{measured}\|^2$$

where '$B_{model}(X_S)$' and '$B_{measured}$' represent a model predicted magnetic vector field where the magnetic vector field where the magnetic sensor is located at '$x_S$', respectively.

13. The method of claim 1, wherein the medical instrument is further associated with a further magnetic sensor, the further magnetic sensor is associated with the predetermined magnet, and the method further comprises:
receiving, from the further magnetic sensor, a further sensor signal representing a further measured axisymmetric magnetic vector field of the magnet, the further measured axisymmetric magnetic vector field having three Cartesian measurement coordinates; and
converting the three Cartesian measurement coordinates of the further measured axisymmetric magnetic vector field into two cylindrical measurement coordinates,
wherein the cost function further comprises a difference between the two cylindrical measurement coordinates of the further measured axisymmetric magnetic vector field and the two cylindrical prediction coordinates of each predicted magnetic vector field.

14. A system for real time in vivo location determination, comprising:
a magnet with an axisymmetric magnetic vector field;
a magnetic sensor configured to be associated with the magnet and to measure the axisymmetric magnetic vector field of the magnet to provide a sensor signal;
a medical instrument configured to be inserted into a patient and to be associated with the magnetic sensor;
a processor configured to be associated with the magnetic sensor;
a storage device configured to be associated with the processor and to store software instructions for causing the processor to:
provide 2-input-2-output artificial neural network (ANN) field model for predicting magnetic vector fields of the magnet, each predicted magnetic vector field having two cylindrical prediction coordinates;
receive, from the magnetic sensor, the sensor signal representing the measured axisymmetric magnetic vector field of the magnet, the measured axisymmetric magnetic vector field having three Cartesian measurement coordinates;
convert the three Cartesian measurement coordinates of the measured axisymmetric magnetic vector field into two cylindrical measurement coordinates;
provide the two cylindrical measurement coordinates as the two inputs to the 2-input-2-output ANN field model;
estimate a relative position between the magnet and the magnetic sensor using the 2-input-2-output ANN field model by minimizing a cost function to produce two cylindrical coordinates as the two outputs of the 2-input-2-output ANN field model, the cost function comprising a difference between the two cylindrical measurement coordinates of the measured axisymmetric magnetic vector field and the two cylindrical prediction coordinates of each predicted magnetic vector field predicted by the 2-input-2-output ANN field model;
convert the two cylindrical coordinates to corresponding three Cartesian coordinates for identifying a location of the medical instrument; and
a display or indicator to show the identified location of the medical instrument within the patient.

15. The system of claim 14 wherein the magnet is passive and untethered.

16. The system of claim 15 wherein the magnet is an axially magnetized Neodymium annular cylinder permanent magnet.

17. The system of claim 14 wherein the model includes weighting coefficients, an order and/or the number of nodes for the magnet and/or a desired error threshold.

18. The system of claim 14 wherein the medical instrument includes the magnet, and the magnetic sensor is further configured to be arranged on or about the patient.

19. The system of claim 14 wherein the medical instrument includes the magnetic sensor, and the magnet is configured to be arranged on or about the patient.

20. The system of claim 14, wherein the software instructions corresponding to providing the ANN field model cause the processor to:
obtain a magnetic vector field map of the magnet;
extract an axis-symmetric field slice from the obtained magnetic vector field map to train or fit the ANN field model; and
determine a number of associated hidden nodes in accordance with a residue error based on the extracted axis-symmetric field slice.

21. The system of claim 14, wherein the cost function, 'C', is:

$$C=\Sigma\|B_{model}(x_S)-B_{measured}\|^2$$

where '$B_{model}(X_S)$' and '$B_{measured}$' represent a model predicted magnetic vector field and a measured magnetic vector field where the magnetic sensor is located at '$X_S$', respectively.

22. The system of claim 14, further comprising:
a further magnetic sensor configured to be associated with the magnet and to further measure the axisymmetric magnetic vector field of the magnet to provide a further sensor signal, wherein the medical instrument and the processor are further configured to be associated with the further magnetic sensor, and the storage device is further configured to store software instructions for causing the processor to:
receive, from the further magnetic sensor, the further sensor signal representing the further measured axisymmetric magnetic vector field of the magnet, the further measured axisymmetric magnetic vector field having three Cartesian measurement coordinates; and
convert the three Cartesian measurement coordinates of the further measured axisymmetric magnetic vector field into two cylindrical measurement coordinates,
wherein the cost function further comprises a difference between the two cylindrical measurement coordinates of the further measured axisymmetric magnetic vector field and the two cylindrical prediction coordinates of each predicted magnetic vector field.

* * * * *